United States Patent [19]

Ciaudelli

[11] Patent Number: 5,084,270
[45] Date of Patent: Jan. 28, 1992

[54] COSMETIC COMPOSITIONS CONTAINING N-ALKOXYALKYLAMIDES

[75] Inventor: Joseph P. Ciaudelli, Ramsey, N.J.

[73] Assignee: Revlon, Inc., New York, N.Y.

[21] Appl. No.: 438,503

[22] PCT Filed: Apr. 21, 1989

[86] PCT No.: PCT/US89/01730
§ 371 Date: Dec. 15, 1989
§ 102(e) Date: Dec. 15, 1989

[87] PCT Pub. No.: WO89/10121
PCT Pub. Date: Nov. 2, 1989

Related U.S. Application Data

[63] Continuation-in-part of Ser. No. 184,858, Apr. 22, 1988, abandoned.

[51] Int. Cl.$^5$ .......................... A61K 7/42; A61K 31/16
[52] U.S. Cl. ........................................ 424/59; 514/625
[58] Field of Search ........................... 514/625; 424/59

[56] References Cited

U.S. PATENT DOCUMENTS

| | | | |
|---|---|---|---|
| 3,230,228 | 1/1966 | Erlemann | 260/295 |
| 3,322,635 | 5/1967 | Erlemann | 514/629 |
| 4,021,572 | 5/1977 | Van Scott | 424/317 |
| 4,105,783 | 4/1978 | Yu et al. | 424/283 |
| 4,197,316 | 4/1980 | Yu | 424/317 |
| 4,234,599 | 11/1980 | Van Scott | 424/279 |
| 4,334,079 | 6/1982 | Schmidt | 564/201 |
| 4,382,765 | 5/1983 | Moller | 424/365 |
| 4,614,784 | 9/1986 | Taya | 514/613 |

FOREIGN PATENT DOCUMENTS

| | | |
|---|---|---|
| 2321752 | 11/1974 | Fed. Rep. of Germany . |
| 2338087 | 1/1975 | Fed. Rep. of Germany . |
| 2632391 | 1/1978 | Fed. Rep. of Germany . |

*Primary Examiner*—Leonard Schenkman
*Attorney, Agent, or Firm*—Julie Blackburn

[57] ABSTRACT

Cosmetic compositions containing N-alkoxyalkylamides for use in providing moisturizing and/or softening properties to treat dry human skin and for use in other cosmetic applications and including also various novel N-alkoxyalkylamides.

18 Claims, No Drawings

COSMETIC COMPOSITIONS CONTAINING N-ALKOXYALKYLAMIDES

CROSS-REFERENCE TO RELATED APPLICATION

This is a continuation-in-part of U.S. patent application Ser. No. 07/184,858, filed April 22, 1988 now abandoned.

FIELD OF THE INVENTION

The present invention relates to N-alkoxyalkylamides and to the use of such compounds in cosmetic compositions, including compositions and processes for providing moisturizing and/or softening properties to human skin, particularly common or mild to moderate "dry skin". The invention will be described initially in connection with its use to treat dry skin conditions. However, as described hereafter, the cosmetic composition of the present invention can be used advantageously for other types of cosmetic applications.

The human skin disorder known as "dry skin" is characterized by cracking, flaking or scaling of the skin of the hands, feet, neck, face or other parts of the body. This disorder may result from a hereditary disorder known as ichthyosis which is a severe form of dry skin. This form of dry skin is not too prevalent. The more common form of "dry skin," which affects a relatively large portion of the population, is a mild to moderate form of dryskin which arises due to exposure to environmental conditions of low humidity in the fall and winter seasons of the temperate climate zones. These environmental conditions give rise to, in skin areas exposed thereto, a loss of moisture from such skin areas, with the attendant formation of fissures, chaps, cracks or flakes in such affected skin areas.

REPORTED DEVELOPMENTS

Various chemical compounds have been proposed for use in combatting such dry skin problems. These compounds are normally formulated with other materials so as to be useful for topical application to the skin in the form of a lotion, cream or ointment.

Examples of such prior art compounds, and the topical compositions in which they may be used for treating dry skin, are disclosed, for example, in U.S. Pat. Nos. 3,230,228; 3,322,635; 4,105,783; 4,197,316; 4,382,765 and W. German OLS 2,632,391. The compounds of these references include some hydroxy-containing carboxylic acid amides.

OBJECTS OF THE PRESENT INVENTION

An object of the present invention is to provide novel compounds useful for the treatment of the mild to moderate form of dry skin.

A further object of the present invention is to provide novel cosmetic compositions based on N-alkoxyalkylamides, including the novel compounds of the present invention and/or known compounds which are useful for a variety of cosmetic purposes, including the treatment of mild to moderate dry skin.

SUMMARY OF THE PRESENT INVENTION

It has now been found that these and other objects of the present invention may be accomplished by the use, for dry skin treating and other cosmetic purposes, of N-alkoxyalkylamides as described below.

Accordingly, one aspect of the present invention comprises a cosmetic composition having, as one of its essential constituents, one or more N-alkoxyalkylamides of the general formula

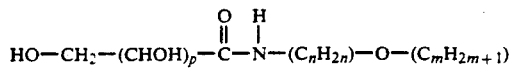

wherein p is a whole number from 1 to about 4,
($C_nH_{2n}$) is a straight or branched chain alkyl bridge in which n is a whole number of 1 to about 6, and is preferably 3, and
($C_mH_{2m+1}$) is a straight or branched chain alkylene group in which m is a whole number of 1 to about 6, and is preferably 1.

For convenience, compounds within the scope of Formula I above are hereafter sometimes referred to as "alkoxyamides". The cosmetic composition of the present invention includes also as an essential constituent a material, hereafter referred to as "a carrier," which is effective in providing the alkoxyamide-containing composition in a form such that the composition can be applied to external portions of the body, for example, the skin.

Another aspect of the present invention comprises novel N-alkoxyalkylamide compounds having the general formula

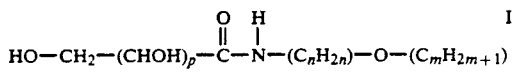

wherein p is a whole number from 1 to 4,
($C_nH_{2n}$) is a straight or branched chain alkyl bridge in which n is a whole number of 1 to 4, and is preferably 3, and
($C_mH_{2m+1}$) is a straight or branched chain alkylene group in which m is a whole number of 1 to 4, and is preferably 1.

The most preferred amide compound of Formula II above is that wherein p is 4, n is 3 and m is 1. Such compound is methoxy propyl gluconamide also referred to hereafter as "MPG",

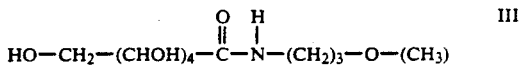

The particularly-preferred MPG exhibits unusually good properties in the cosmetic composition of the present invention as will be discussed more fully below, and as is exemplified by use of various of the exemplary compositions set forth below.

Another aspect of the present invention comprises a process in which one or more compounds of Formula I above or a cosmetic composition comprising one or more compounds of Formula I above and a carrier therefor is applied to an external portion of the body for the purpose of cosmetically treating said body portion, for example, for the purpose of moisturizing and softening the human skin.

The term "cosmetic composition" is used herein in its usually understood sense, that is, to define a composition which is applied to external body portions, typically a human body, for beautifying, cleansing, moisturizing or otherwise treating the external surface of the body, including by cleansing, coloring, conditioning, or protecting the external surface of the body part such as, for example the skin and hair. Examples of cosmetic compositions in which the alkoxyamides of the present invention can be used are skin moisturizers, sun screens, makeup, protein concentrates, skin firming compositions and cleansers, including decongestant cleansers.

The cosmetic composition of the present invention is to be distinguished from pharmaceutical compositions of the type disclosed in West German OLS No. 2,321,752 and its Patent of Addition OLS No. 2,338,087. These patents disclose various acid amides, including an acid amide within the scope of Formula I above, for use in a variety of applications other than cosmetic applications, including use in pharmaceutical compositions. The German patents disclose that the pharmaceutical compositions described therein are in a form for oral, parenteral, or rectal administration, that is, in a form such that the pharmaceutical composition is capable of entering the body. In contrast, the cosmetic composition of the present invention is in a form such that it can be applied to the exterior of the body and does not enter the interior of the body, that is, it does not pass beyond the basal membrane of the skin. The term "applied cosmetically" (or variant thereof) as used herein in connection with the application of an alkoxyamide or of the cosmetic composition of the present invention to an external body portion means that the alkoxyamide is in a form such that none of it or a therapeutically ineffective amount of it passes beyond the basal membrane.

Advantages associated with the present invention are ease of manufacture and handling, and the novel alkoxyamides have a neutral pH, enabling the use of a neutral pH carrier Most prior art moisturizers, such as aliphatic hydroxyacids, are acidic, and must be neutralized or incorporated into a basic carrier to be effective and non-irritating to human skin. The alkoxyamides are also easily handled and stored, as they are generally in the form of a plain white powder. They are also water-soluble, enabling them to be easily incorporated into water-based compositions. They can also be easily manufactured by known methods from readily available precursors.

DETAILED DESCRIPTION OF THE INVENTION

As mentioned above, the essential ingredients of the cosmetic compositions of the present invention are one or more of the alkoxyamides of Structure I above and a carrier therefor. For many applications, the composition will include one or more additional ingredients, the identity of which will depend on the intended use of the composition and the selection of which can be made in accordance with available knowledge in the art.

The alkoxyamides of Structure I can be prepared by any suitable method. The aforementioned OLS Nos. 2,321,752 and 2,338,087 contain information on preparing compounds within the scope of Structure I.

In preferred form, the Structure I compounds of the present invention are prepared by reacting one mole of an amine compound having the structure $$H_2N-(C_nH_{2n})-O-(C_mH_{2m+1}) \quad IV$$

wherein $(C_nH_{2n})$ and $(C_mH_{2m+1})$ are as defined above in Structure I,
with one mole of a carboxylic acid or lactone having one of the structures $$HO-CH_2-(CHOH)_q-\overset{O}{\underset{\|}{C}}-OH, \text{ or} \quad V$$

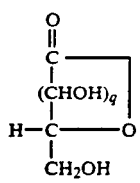
VI wherein q is a whole number of 1 to 3.

The preferred of such Structure IV amine compounds is methoxy propyl amine, i.e. wherein m is 1 and n is 3.

The preferred of such Structure V carboxylic acids is gluconic acid.

The preferred of such Structure VI lactones is glucono-delta-lactone, i.e. wherein q is 3.

In reacting the Structure IV amine with the Structure V/VI acid/lactone, an excess of the amine is usually used to help drive the reaction to completion. Such excess is usually in the amount of about 0.1 to about 0.5 mole %.

The lactone/acid is first heated with stirring in a refluxing alcoholic solvent, at atmospheric pressure, to slurry the solids. The alcohol used is aliphatic and has a reflux temperature of about 65 to about 86° C. Then the amine is added dropwise to the slurry, in the refluxing solvent, and the solids therein are dissolved to produce a light yellow colored solution. The reaction takes about 10 to 30 minutes at reflux temperatures. The reaction is slightly exothermic. Any temperature rise, however, is only noticeable when the amine is added at room temperature, but is not detectable at solvent reflux temperatures. The heating is then discontinued and the solution is allowed to cool with stirring. A precipitate generally starts to form approximately 20 degrees below the refluxing temperature of the solvent. Upon reaching room temperature (~25° C.), the solids are then filtered off using a Buchner funnel under vacuum. The solids are washed with alcohol solvent. Yields of about 90 to about 98% of the N-alkoxyalkylamides of the hydroxyacids are thus obtained after drying.

The carrier for use in formulating the composition of the present invention can comprise one or more compounds which will be selected based on the particular intended use of the composition. Speaking generally, the carrier functions to permit formulation of a composition that allows the alkoxyamide to be applied to an exterior body surface in the desired way. The carrier may be inorganic or organic in nature, and like the alkoxyamide, it must be non-toxic and non-irritating and should also be inoffensive to the user. The carrier must, of course, be compatible with the alkoxyamide. Examples below are illustrative of a variety of carriers that can be used.

In addition to the essential ingredients described above, the composition of the present invention can include also one or more optional ingredients, also referred to herein as "auxiliary components." Examples of auxiliary components are lubricants, preservatives, perfumes and colorants It is believed that the composition of the present invention will be used most widely in applications that are designed for use in treating humans having a dry skin condition. Accordingly, at least one of the active ingredients used in such compositions for such purposes will comprise one or more of the Structure I compounds disclosed above, and most preferably the compound of Structure III.

The composition of the present invention may be used for prophylactic as well as therapeutic purposes, relative to their proposed use in treating dry skin by the topical application thereto, so as to prevent or cure the occurrence of any cracking, flaking, scaling or chapping of the skin. Thus, the compositions of the present invention may be used to prevent, cure, or ameliorate dry skin conditions, acne, psoriasis, seborrhea, keratose, diaper rash, sunburn and windburn.

The compositions of the present invention may be prepared and used in the form of a lotion, cream, ointment, stick, soap, or other forms commonly employed in the art of cosmetic, including skin care, formulations. They are preferably used in an emulsified form.

For use in treating dry skin, the compositions of the present invention are prepared employing skin-softening and moisturizing effective amounts (for example, up to about 25 wt.%) of one or more of the alkoxyamide compounds of the present invention in a cosmetically acceptable carrier, such as a hydrophilic ointment (USP) or petrolatum. When used in such compositions, preferably about 1 to about 20, and most preferably about 5 to about 15, weight % of the alkoxyamide compound(s) are used therein. It should be understood that smaller amounts of the alkoxyamide can be used in compositions within the scope of the present invention, for example, in compositions which include one or more other skin-moisturizers or softeners or when used in compositions that are designed primarily for other types of cosmetic functions. This is discussed more fully below.

When an aqueous carrier is utilized, the bulk of such compositions of the present invention will comprise about 30 to about 75, and preferably about 55 to about 65, weight % of distilled water, and about 10 to about 40, and preferably about 15 to about 30 weight %, of a combination of other commonly used cosmetically effective auxiliary components of the various types of compositions in question (i.e., lotion, cream, ointment stick or soap). It should be understood however, that the water in the composition can be totally or partly eliminated by the use of non-aqueous or partially aqueous carriers. Typically the auxiliary components are chemically inert with respect to each other, and with respect to the alkoxyamide compounds of the present invention The following is exemplary of aqueous compositions of the present invention for dry skin applications (weight %, based on total weight of the composition):
about 0.75 to about 7 % emulsifying agents
about 3 to about 15 % emollients
about 1 to about 2 % medicament of the present invention
about 0.1 to about 5% lubricant
about 0.2 to about 1% preservative
about 0.2 to about 1% perfume
about 0.01 to about 0.1% colorant —remainder, water.

Lists of carriers and auxiliary components, which are well known in the art, are disclosed, for example, in
"Cosmetics: Science and Technology," Edited by M. S. Balsam and E. Sagarin, 2nd Edition, 1972, Wiley Pub. Co.;

"The Chemistry and Manufacture of Cosmetics" by M. G. DeNavasse; and
"Harry's Cosmeticology," J. B. Wilkinson et al., 7th Edition, 1982, Chem. Pub. Co.; the disclosures of each of the above being incorporated herein by reference.

The alkoxyamide compounds themselves can be topically applied cosmetically in uncompounded form to the areas of the skin to be treated therewith Whether used as is, or in compounded or compositional form, for dry skin treating purposes, the alkoxyamide compounds of the present invention ar ®topically applied one or more, and preferably about 2 to 4, times per day to the area of skin to be treated therewith for a period of about 7 to 21 days in order to achieve the desired amelioration of the dry skin condition.

As mentioned above, the alkoxyamides can be used effectively also in applications that are designed primarily to treat conditions other than dry skin conditions, for example, in makeup, cleansers, sunscreens, self-tanning and lightening compositions, skin firmers, shaving preparations, shampoos, topically applied therapeutic compositions and depilatories. For use in such applications, the alkoxyamides can be used in quite small amounts.

Makeup compositions, for example, can effectively incorporate the alkoxyamide in small amounts, generally about 0.01 to about 5 wt.%, preferably about 0.02 to about 0.1 wt.% of the composition. In addition, makeup compositions of the present invention generally comprise about 1 to about 40 wt.%, preferably about 10 to about 20 wt.%, of a coloring agent (for example, pigment) in a suitable carrier Suitable pigments include all inorganic and organic pigments which are usable in cosmetic formulations. Examples include carmine, bismuth oxychloride, zinc oxide, ferric oxide, ferrous oxide, kaolin, ultramarine violet, ultramarine blue, chromium oxide, chromium hydroxide, silica and manganese violet. Other examples include lakes of organic colorants such as FD&C Red No. 7 calcium lake, FD&C Yellow No. 5 aluminum lake, FD&C Red No. 9 barium lake and FD&C Red No. 30. Additional examples include talc, mica, and titanium oxide: any of the foregoing carried on the surface of talc, mica or titanium oxide; and titanated mica. Unless stated otherwise, the term "pigment" includes within its meaning a mixture of two or more pigments.

Examples set forth below show the use of the alkoxyamides in various types of the compositions referred to above.

The compounds of the present invention may be stored as is, or in the form of the compositions disclosed herein, in closed containers at room temperature for extended periods of time without a change in their utility for dry skin treating purposes.

The following examples are merely illustrative of the scope of the present invention and are not intended as a limitation upon the scope thereof.

EXAMPLE 1

Glucono delta lactone (352 grams) was heated in 1000 ml of isopropyl alcohol to reflux temperatures about B6° C (at atmospheric pressure), in a two-liter-3 neck-glass flask equipped with a stirrer, reflux condenser column and a stoppered inlet port. Then 180 grams of methoxy propyl amine was added to the refluxing lactone slurry over a period of about 10 minutes through the inlet port.

The resulting system was then stirred and heated at reflux (~86° C.) for an additional 10 minutes, and then the heat was turned off. At this temperature (~86° C.) all the components of the system were dissolved in the isopropyl alcohol. As the system cooled a precipitate started to form at approximately 65° C.

When the temperature of the system reached ambient temperature (~25° C.), the system was filtered through a Buchner funnel under vacuum (house) and the filtrate was recovered. The solid was transferred to a pyrex dish for air drying (over about 6 hours). A yield of 510 grams of product (methoxy propyl gluconamide) was thus obtained, for a yield of 95.86% of the theoretical.

An additional amount of such product, 12 grams, was also obtained after distilling off ~90% of the isopropyl alcohol form the filtrate that passed through the filter.

The two portions of the recovered solids were blended together and about 100 grams of the thus recovered solids were recrystallized in water and isopropyl alcohol.

An analysis of such product showed that it contained 5.17% nitrogen, as compared to 5.18% theoretical. The compound had a melting point of 107.5° C. The IR spectrum of the compound showed significant bands at 3500, 3400, 3340, 2920, 2880, 1650, 1535, 1430, 1240, 1180, 1095, 1070, 1035, 730 and 630 reciprocal centimeters ($cm^{-1}$). These bands are characteristic of hydroxy stretch, nitrogen-hydrogen stretch, methyl stretch, methoxy stretch, methoxy stretch and various secondary amide bands.

EXAMPLES 2 to 3

Two cream formulations (in 1 kilogram batches each) were prepared to comparatively evaluate the compound made in Example 1 as a skin moisturizing or softening material. The creams were emulsions prepared as described below. These two formulations, in weight %, were as follows:

| Component | Weight % of Component Example | |
|---|---|---|
| | 2 | 3 |
| Water | 70.36 | 70.36 |
| Propylene Glycol | 1.00 | 1.00 |
| Methyl p-Hydroxybenzoate | 0.30 | 0.30 |
| Mineral Oil | 1.50 | 1.50 |
| $C_{12-15}$ Alcohol Benzoate | 1.50 | 1.50 |
| Glyceryl Monostearate | 2.30 | 2.30 |
| Polawax* | 4.08 | 4.08 |
| Stearyl Alcohol | 1.50 | 1.50 |
| Polyoxyethylene 21 Stearyl Ether | 0.75 | 0.75 |
| Silicone Oil | 0.21 | 0.21 |
| Stearyl Stearoyl Stearate | 1.00 | 1.00 |
| Propyl p-Hydroxybenzoate | 0.10 | 0.10 |
| Bisabolol | 0.20 | 0.20 |
| Imidazolidinyl Urea | 0.20 | 0.20 |
| Methoxy Propyl Gluconamide | — | 15.00 |
| Glucono Delta Lactone | 15.00 | — |
| TOTAL | 100.00 | 100.00 |

*Polawax (Croda, Inc.) is a preparation of higher fatty alcohols and ethylene oxide reaction products.

Both emulsions were prepared from four (4) subcombinations, or phases, of the components listed above.

Phase A is made of 52.36% water, 1.00% propylene glycol and 0.30% methyl-p-hydroxy benzoate.

Phase D is made of 15.00% water and 15.00% of the additive being comparatively evaluated, i.e., methoxy propyl gluconamide or glucono delta lactone.

Phase B contains all the remaining components except the imidazolidinyl urea.

The components of Phase A are first mixed together with heating at 80° C., and the components of Phase B are also mixed together at 80° C. Then Phase B is added to Phase A and heating (at 80° C.) and mixing is continued for about 10 minutes and then the heating is stopped.

Phase C is formed by dissolving the imidazolidinyl urea in the water and heating to 50° C. Phase C is then added to the Phase A/B admixture. Phase D is made by dissolving the additive of choice in water and heating to 45° C, then Phase D is added to the Phase A/B/C admixture. The resulting product is then cooled to 35° C. with mixing and packaged.

The formulations of Examples 2 to 3 were comparatively evaluated by a text panel of 10 panelists with dry skin.

In evaluating the test formulations, the panelists cleansed both of their forearms with their regular soap once in the morning and once in the evening and than applied the test formulation to one forearm. The other forearm was left untreated as a control. Each formulation was thus tested twice daily for a two week period. At the end of this time, the forearms of each panelist were compared. The results showed that although the formulation of Example 2 provided some amelioration of the dry skin condition of the treated forearms, as compared to the untreated forearms, the use of the formulation of Example 3 provided a noticeably improved difference in its effect on the dry skin of the forearms treated therewith as compared to the effect provided by the use of the formulation of Example 2.

EXAMPLE 4

This example illustrates the compatibility of methoxy propyl gluconamide with other cosmetic ingredients including sunscreening agents.

| Component | Weight % |
|---|---|
| Water | 62.125 |
| Methyl Paraben | 0.250 |
| Propylene Glycol | 5.000 |
| Carbomer 941 | 0.125 |
| Triethanolamine | 0.100 |
| Glyceryl Stearate and Laureth-23 (polyoxyethylene ether) | 8.000 |
| Cetyl Alcohol | 1.500 |
| Methyl Paraben | 0.150 |
| Butylated Hydroxy Anisole | 0.150 |
| $C_{12-15}$ Alcohol Benzoate | 5.000 |
| Ethyl Hexyl Linoleoyl Oxystearate | 5.000 |
| Bisabolol | 0.200 |
| Glycol Stearate | 3.000 |
| Dimethicone | 1.000 |
| Polyoxyethylene 21 Stearyl Ether | 0.750 |
| Octyl Dimethyl PABA | 3.000 |
| Benzophenone-3 | 1.500 |
| Dimethylol Dimethyl Hydantoin | 0.400 |
| Perfume | 0.250 |
| Methoxy Propyl Gluconamide | 2.500 |
| TOTAL | 100.000 |

The methoxy propyl gluconamide was physically, chemically and functionally compatible with the other components of the Example 4 formulation. The use of the methoxy propyl gluconamide in the Example 4 formulation provides noticeably improved dry skin treating properties as compared to the use of the same formulation without such amide therein. The formulation is also useful for sunscreening purposes.

EXAMPLE 5

The following illustrates the compatibility of the subject amide compound in a water in oil emulsion furmulation.

| Component | Weight % |
|---|---|
| Water | 52.058 |
| Methyl Paraben | 0.200 |
| Ethyl Paraben | 0.150 |
| Disodium Salt of Ethylene Diamine Tetraacetic Acid | 0.240 |
| Butylated Hydroxy Anisole | 0.150 |
| Propylene Glycol | 4.000 |
| Triethanolamine | 0.092 |
| Cyclomethicone | 10.000 |
| Carbopol 1342 (Carbomer 1342) | 0.110 |
| Dimethicone 50 cs | 10.000 |
| Dimethicone 1000 cs | 7.500 |
| Isocetyl Linoleoyl Oxystearate | 5.000 |
| *Abil ® WSO8 | 5.000 |
| Phenoxyethanol | 0.500 |
| Methoxy Propyl Gluconamide | 5.000 |
| TOTAL | 100.000 |

*Abil ® WSO8 (Goldschmidt AG) is a combination of Cetyl Dimethicone Copolyol Cetyl Dimethicone, Polyglyceryl-3 Oleate and Hexyl Laurate.

The methoxy propyl gluconamide was physically, chemically and functionally compatible with the other components of the Example 5 formulation. The use of the methoxy propyl gluconamide in the Example 5 formulation provides noticeably improved dry skin treating properties as compared to the use, for such purposes, of the same formulations without such amide therein.

The next example is illustrative of a skin moisturizer of the present invention.

| Ingredient | Ex. 6, wt. % |
|---|---|
| Methoxy propyl gluconamide | 0.1 |
| Water | 55.67 |
| Carbomer 941 | 8 |
| Octyl methoxycinnamate | 7 |
| Butylene glycol | 5 |
| Propylene glycol | 4 |
| Dicaprylate/dicaprate | |
| Stearic acid | 3 |
| Benzophenone-3 | 3 |
| Isostearyl neopentanoate | 2.5 |
| Glycerin | 2 |
| Triethanolamine | 1.85 |
| Glyceryl stearate | 1.5 |
| Polysorbate 60 | 1.2 |
| Petrolatum | 1 |
| Coco-caprylate/caprate | 1 |
| Dimethicone | 0.5 |
| Sorbitan stearate | 0.5 |
| Squalane | 0.5 |
| Sodium hyaluronate, chitin | 0.5 |
| Imidazolidinyl urea | 0.3 |
| Cetyl alcohol | 0.25 |
| Methylparaben | 0.15 |
| Tocopheryl acetate | 0.1 |
| Sodium PCA (2-pyrrolidone-5-carboxylic acid) | 0.1 |
| Evening primrose oil | 0.1 |
| Propylparaben | 0.05 |
| Bisabolol | 0.05 |
| Trisodium EDTA | 0.05 |
| Fragrance | 0.03 | compositions for firming, plumping or tightening the skin can incorporate advantageously the alkoxyamide. Such compositions can comprise also a skin-firming agent such as, for example, xanthan gum, carboxy methyl cellulose or related cellulosic material, and fibronectin or other proteinaceous material, and a compatible carrier. The skin-firming agent will generally comprise about 0.1 to about 35 wt.%, preferably about 2 to about 15 wt.%, of the total composition. The alkoxyamide will generally comprise about 0.1 to about 20 wt.%, preferably about 1 to about 15 wt.%, of the total composition. Tables 1 and 2 below identify the ingredients and concentrations of eight skin-firming compositions of the present invention.

TABLE 1

| Ingredient, wt. % | Ex. 7 | Ex. 8 | Ex. 9 | Ex. 10 | Ex. |
|---|---|---|---|---|---|
| Methoxy propyl gluconamide | 2.5 | 2.5 | 2.5 | 2.5 | 2.5 |
| Water | 43.5 | 41.5 | 37.6 | 37.6 | 41.6 |
| 2-phenylimidazole-5-sulfonic acid | 15 | 15 | 15 | 15 | 15 |
| Magnesium aluminum silicate, 6% sol'n | 13.3 | 14.3 | 16.3 | 16.3 | 17.3 |
| Cyclomethicone | 10 | 11 | — | 9 | 9 |
| Dimethicone | — | — | 9 | — | — |
| Propylene glycol ceteth-3 acetate | 10 | 10 | 10 | 10 | 10 |
| Glycereth-7 triacetate | — | 1 | 5 | — | — |
| Arnica extract, barley extract and hydrolyzed marine polypeptides* | 2.5 | 2.5 | 2.5 | 2.5 | 2.5 |
| Isopropyl PPG-2-isodeceth-7-carboxylate | — | — | — | 5 | — |
| Biospheres** | 1 | 1 | 1 | 1 | 1 |
| Titanium dioxide/propylene glycol, 25% sol'n | — | — | 1 | 1 | — |
| Methyl gluceth-10 | 1 | — | — | — | — |
| Sodium hyaluronate, chitin | 0.5 | 0.5 | — | — | — |
| Sodium hyaluronate, polyquaternium-24 | — | — | 0.4 | 0.4 | 0.4 |
| Xanthan gum | 0.4 | 0.4 | 0.4 | 0.4 | 0.4 |
| Imidazolidinyl urea | 0.3 | 0.3 | 0.3 | 0.3 | 0.3 |

*Available from Laboratories Serobiologiques as Firmogen LS 3497
**Firmogen LS 3497 and methoxy propyl gluconamide encapsulated in soluble animal collagen and chondroitin sulfate by Bioetica

TABLE 2

| Ingredient, wt. % | Ex. 12 | Ex. 13 | Ex. 14 |
|---|---|---|---|
| Methoxy propyl gluconamide | 1 | 10 | 5 |
| Water | 81.65 | 57 | 68 |
| Chitin extract | 5 | 10 | 2.5 |
| Fibrosomes* | 1 | 3 | 10 |
| Arnica extract, barley extract and hydrolyzed marine polypeptides | 1 | 5 | 3 |
| Carbomethoxy cellulose | 0.3 | 0.8 | 1 |
| Xanthan gum | 0.3 | 0.2 | 0.6 |
| Acetamide MEA | 4 | 5 | 3.5 |
| Butylene glycol | 2.5 | 3 | 2 |
| PPG-24-Glycereth-24 | 1 | 2 | 2 |
| PVP/VA E-335 | 1 | 2 | 1 |
| Simethicone | 0.5 | 1 | 0.5 |
| Methylparaben | 0.2 | 0.3 | 0.2 |
| Ethylparaben | 0.1 | 0.1 | 0.1 |
| Propylparaben | 0.1 | 0.05 | 0.05 |
| Polysorbate-20 | 0.1 | 0.3 | 0.2 |
| Trisodium EDTA | 0.1 | 0.1 | 0.1 |
| Diazolidinyl urea | 0.1 | 0.1 | 0.2 |
| Fragrance | 0.05 | 0.05 | 0.05 |

*Fibronectin-containing liposomes

Alkoxyamides are ideal for use in products used for skin tanning type applications where their superior moisturizing properties aid in preventing drying of the skin caused by exposure to the sun and/or wind. The essential components for a sunscreen formulation of the present invention comprise a sunscreening agent, the alkoxyamide and a suitable carrier.

There are many sunscreening agents available. As skin tanning is caused primarily by exposure to ultraviolet radiation, it is essential that an effective sunscreening agent protect the skin from radiation in the ultraviolet range. Commonly used sunscreening agents include: p-aminobenzoic acid (PABA) and derivatives such as octyl dimethyl PABA, amyl-p-dimethylaminobenzoate and glyceryl monop-aminobenzoate; cinnamates such as octyl methoxycinnamate, isobutyl salicylcinnamate and 2-ethoxyethyl-p-methoxycinnamate; benzophenone and derivatives such as 2-hydroxy-4-methoxybenzophenone (benzophenone-3) and 2-hydroxy-4-methoxybenzophenone-5-sulfonic acid (benzophenone-4); salicylates such as benzyl salicylate, homomenthyl salicylate, dipropylene glycol salicylate and 2-ethylhexyl salicylate; ricinoleate and derivatives such as propylene glycol ricinoleate; coumarin (2H-1-benzopyran-2-one); tannic acid and digalloyl trioleate.

The concentration of the sunscreening agent depends on its efficacy as a sunscreen, but is generally about 0.25 to about 33 wt.%, preferably about 1 to about 15 wt.%, of the total weight of the composition. The amount of the alkoxyamide comprises preferably about 0.01 to about 10 wt.%, and most preferably about 0.1 to about 5 wt.%, of the total weight of the composition.

Table 3 below identifies the ingredients and concentrations of four sunscreen compositions of the present invention. The term in parentheses is the approximate Sun Protection Factor (SPF) for each composition. Examples 15 to 17 are aqueous-based compositions, while Example 18 is a non-aqueous composition.

TABLE 3

| Ingredient, wt. % | Ex. 15 (SPF-8) | Ex. 16 (SPF-15) | Ex. 17 (SPF-25) | Ex. 18 (SPF-25) |
|---|---|---|---|---|
| Methoxy propyl gluconamide | 0.1 | 0.1 | 0.1 | 0.025 |
| Water | 42.1 | 42 | 32.1 | — |
| Octyl methoxycinnamate | 6 | 7.5 | 5 | 7.5 |
| Benzophenone-3 | 2 | 6 | 6 | 3.2 |
| Octyl dimethyl PABA | — | — | 8 | — |
| Octyl palmitate | 11.4 | — | 10 | — |
| Mineral Oil | 6 | — | 6.2 | 9.9 |
| Glycerin | 2 | 0.5 | 2 | — |
| Petrolatum | — | — | — | 28.25 |
| Microcrystalline Wax | — | — | — | 14.5 |
| Carbomer 940, 2.5% sol'n | 12 | 12 | 12 | — |
| Phenyl trimethicone | 4 | 8.3 | 4 | — |
| Dimethicone | 1 | 1 | 1 | — |
| Methylparaben | 0.25 | 0.25 | 0.25 | 0.1 |
| Propylparaben | 0.15 | 0.15 | 0.15 | 0.2 |
| Butylparaben | — | — | — | 0.1 |
| Stearic acid | 2.6 | 1 | 2.6 | — |
| Stearyl alcohol | 2 | 2.25 | 2 | — |
| Trioctyl citrate | — | 6 | — | — |
| Hydrogenated polyisobutene | — | 4 | — | — |
| Ozokerite | — | — | — | 6.5 |
| Tin oxide | — | — | — | 7.5 |
| Unsaponifiable shea butter | — | — | — | 6 |
| Myristyl myristate | — | — | — | 5.75 |
| Hydroxylated lanolin | — | — | — | 3.75 |
| C10–C30 Cholesterol/ Lanosterol esters | — | — | — | 4 |
| DEA-Cetyl phosphate | 2.5 | 2.5 | 2.5 | — |
| Aloe extract | 1 | — | 1 | 1.3 |
| PVP/Eicosene copolymer | 2 | 3 | 2.25 | — |
| PVP, 20% solution | — | 1.5 | — | — |
| Shea butter | 0.5 | — | 0.5 | — |
| Triethanolamine | 0.28 | 0.37 | 0.28 | — |
| Tocopheryl acetate | 0.3 | 0.2 | 0.3 | 0.15 |
| Diazolidinyl urea | 0.3 | 0.3 | 0.3 | — |
| Panthenol | 0.2 | 0.05 | 0.2 | — |
| Hydrolyzed animal elastin | 0.2 | 0.1 | 0.2 | — |
| Allantoin | 0.1 | 0.1 | 0.1 | — |
| Allantoin Urocanate | 0.05 | 0.05 | 0.05 | 0.05 |
| Histidine | 0.1 | 0.1 | 0.1 | — |
| Tyrosine | 0.05 | 0.05 | 0.05 | — |
| Arnica extract, barley extract and hydrolyzed marine polypeptides | 0.1 | 0.1 | 0.1 | 0.025 |
| Trisodium EDTA | 0.1 | 0.1 | 0.1 | — |
| Propylene glycol, citric acid, BHA, propyl gallate | 0.1 | — | 0.1 | — |
| Fragrance | 0.5 | 0.5 | 0.5 | — |
| Benzoic acid | — | — | — | 0.3 |
| C30–C46 Piscine oil | — | — | — | 0.02 |
| Bisabolol | — | — | — | 0.05 |
| Iron oxide pigments | — | — | — | 0.65 |

The alkoxyamide can also be used advantageously in self-tanning compositions. Such compositions contain tanning agents capable of darkening the skin without exposure to ultraviolet radiation. The preferred, and most commonly used, tanning agent is dihydroxyacetone, which generally comprises about 1 to about 12 wt.%, preferably about 2 to about 7 wt.%, of the total composition. The alkoxyamide will generally comprise about 0.01 to about 10 wt.%, preferably about 0.1 to about 5 wt.%, of the total composition. Table 4 below identifies the ingredients from which Example 19, a self-tanning composition, was made.

TABLE 4

| Ingredient | wt. % |
|---|---|
| Methoxy propyl gluconamide | 0.1 |
| Water | 73.15 |
| Dihydroxyacetone | 5 |
| Mineral oil | 10 |
| Glyceryl stearate/PEG-100 stearate | 6 |
| Propylene glycol | 2 |
| Cetyl alcohol | 1.2 |
| Stearic acid | 0.75 |
| Dimethicone | 0.5 |
| Diazolidinyl urea | 0.3 |
| Sorbic acid | 0.15 |
| Methylparaben | 0.15 |
| Propylparaben | 0.1 |
| Arnica extract, barley extract and hydrolyzed marine polypeptides | 0.1 |
| Fragrance | 0.5 |

The alkoxyamide can also be used advantageously in compositions for treating the skin before or after exposure to tanning radiation. Such compositions contain at least one moisturizer, and do not require sunscreens or self-tanning agents. Optional ingredients include antioxidants such as tocopheryl acetate (vitamin E), healing agents such as allantoin, protein extracts and amino acid preparations. The alkoxyamide will generally comprise about 0.01 to about 10 wt.%, preferably about 0.1 to about 5 wt.%, of the total composition. Table 5 below identifies the ingredients from which Example 20, a pre-tanning conditioner, was made.

TABLE 5

| Ingredient | wt. % |
|---|---|
| Methoxy propyl gluconamide | 0.1 |
| Water | 63.33 |
| Hydroxypropyl methylcellulose, 3% sol'n | 13.66 |
| Glycerin | 4.88 |
| PPG-3 Myristyl ether | 3.90 |
| Glyceryl stearate, stearamidoethyl diethylamine | 3.42 |
| Acetylated lanolin | 1.95 |
| Mineral oil, lanolin alcohol | 1.46 |
| Shea butter | 1 |
| Aloe extract | 1 |
| Cetyl alcohol | 0.83 |
| Steapyrium chloride | 0.78 |
| Dimethicone | 0.73 |
| PEG-40 Stearate | 0.55 |
| Hydrogenated vegetable oil | 0.49 |
| Diazolidinyl urea | 0.2 |
| Tocopheryl acetate | 0.2 |
| Panthenol | 0.2 |
| Hydrolyzed animal elastin | 0.2 |
| Methylparaben | 0.2 |
| Sorbitan tristearate | 0.14 |
| Arnica extract, barley extract and hydrolyzed marine polypeptides | 0.1 |
| Histidine | 0.1 |
| Allantoin | 0.1 |
| Propylparaben | 0.1 |
| Benzathonium chloride | 0.07 |
| Allantoin urocanate | 0.05 |
| Tyrosine | 0.05 |
| Fragrance | 0.25 |

The alkoxyamide can be incorporated into skin cleaning compositions to reduce drying out the skin by washing. Essential components of such compositions include also a detergent, or cleansing agent, such as cocamidopropyl betaine, sodium lauryl (and laureth) sulfate and sucrose cocoate, and a compatible carrier. The cleansing agent generally comprises about 1 to about 20 wt.%, preferably about 2 to about 11 wt.%, of the total composition, based on the solids content of the cleansing agents, which usually are aqueous solutions. The alkoxyamide will generally comprise about 0.1 to about 10 wt.%, preferably about 0.5 to about 5 wt.%, of the total composition. Other desired properties in the composition can be realized by incorporating suitable ingredients, and the cleanser can be formulated for different types of skin. Table 6 below identifies the ingredients and concentrations from which Examples 21-23, all decongestant cleansers, were made. Example 21 is formulated for normal skin, Example 22 for dry skin, and Example 23 for oily skin.

TABLE 6

| Ingredient, wt. % | Ex. 21 | Ex. 22 | Ex. 23 |
|---|---|---|---|
| Methoxy propyl gluconamide | 1.0 | 1.0 | 0.5 |
| Carbomer 1342, 1.8% sol'n | 34.72 | — | 69.58 |
| Carbomer 940, 2.5% sol'n | 25 | 30 | — |
| Water | 17.89 | 46.11 | 5.43 |
| Propylene glycol | 6.3 | 7 | 2.61 |
| Sodium lauryl sulfate 30% sol'n | 6 | 3.5 | 4.38 |
| Sucrose cocoate, 30% sol'n | 3 | 3.5 | — |
| Cocamidopropyl betaine, 35% sol'n | 1 | 3.5 | 8 |
| Triethanolamine | 2.13 | 1.28 | 2.05 |
| PEG-150 Distearate | — | 1 | — |
| Sodium laureth sulfate, 30% sol'n | 1 | — | 5.7 |
| acrylates copolymer | 1 | 1 | 1 |
| Sodium chloride | 0.25 | 0.25 | — |
| Methylparaben | 0.2 | 0.25 | 0.2 |
| DMDM Hydantoin | 0.2 | 0.2 | 0.2 |
| Glycerin | 0.1 | 0.1 | 0.1 |
| Sodium PCA | 0.1 | 0.1 | 0.1 |
| Propylparaben | 0.05 | 0.05 | 0.05 |
| Fragrance | 0.06 | 0.06 | 0.1 |
| FD & C Red-4, Yellow-5, Blue-1, 2% sol'n | 0.06 | 0.04 | 0.04 |

The alkoxyamide can be incorporated into compositions containing proteinaceous material applied to the skin. Examples of such proteinaceous material include protein and protein concentrates of such proteins such as collagen, fibronectin, elastin, marine protein and animal protein. The phrase "proteinaceous material," as used herein, includes also partially and fully hydrolyzed forms thereof, for example, polypeptide fragments and substituent amino acids. The proteinaceous material generally comprises about 0.1 to about 50 wt.%, preferably about 1 to about 15 wt.%, of the total composition. The alkoxyamide will generally comprise about 0.01 to about 10 wt.%, preferably about 0.1 to about 3 wt.%, of the total composition. Table 7 below identifies the ingredients and concentrations from which Example 24, a collagen concentrate, was made.

TABLE 7

| Ingredient | Wt. % |
|---|---|
| Methoxy propyl gluconamide | 0.5 |
| Water | 39.59 |
| Algae extract | 37 |
| Soluble animal collagen | 10 |
| Animal collagen amino acids | 0.2 |
| TEA Salicylate | 6.67 |
| Propylene glycol | 3 |
| Polysorbate-20 | 1.5 |
| Diazolidinyl urea | 0.5 |
| Arnica extract, barley | 0.5 |

TABLE 7-continued

| Ingredient | Wt. % |
|---|---|
| extract and hydrolyzed marine polypeptides | |
| Methylparaben | 0.2 |
| Glycosaminoglycans | 0.05 |
| Sodium polyglutamate | 0.05 |
| Fragrance | 0.2 |
| FD & C Yellow-5, 1% sol'n | 0.04 |

In summary, it can be said that the present invention affords the means for providing improved cosmetic compositions which can be tailor made into a variety of different types of formulations to suit particular needs.

What is claimed is:

1. A cosmetic composition for external application to human skin comprising:

(A) up to 25% by weight of one or more compounds of the formula

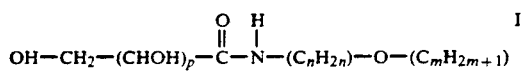

wherein p is a whole number from 1 to about 4, $(C_nH_{2n})$ is a straight or branched chain alkyl bridge in which n is a whole number of 1 to about 6, and $(C_mH_{2m+1})$ is a straight or branched chain alkyl group in which m is a whole number of 1 to about 6 and (B) the remainder a topical carrier selected from the group consisting of lotion, cream, ointment, and make-up base containing a cosmetically acceptable pigment.

2. A composition according to claim 1 including the Formula I compound in which p is 4.

3. A composition according to claim 1 including the Formula I compound in which n is 3.

4. A composition according to claim 1 including the Formula I compound in which m is 1.

5. A composition according to claim 1 including the Formula I compound in which m is 1.

6. A composition according to claim 1 including the Formula I compound in which p is 4, n is 3, and m is 1.

7. A composition according to claim 1 and effective for moisturizing and softening human skin which comprises a skin moisturizing and softening amount of at least one of the Formula I compounds.

8. A composition according to claim 6 and effective for moisturizing and softening human skin including a skin moisturizing and softening amount of the Formula I compound.

9. A composition according to claim 1 comprising 0.1-20 wt.% of the Formula I compound and 0.1-35 wt.% of a skin-firming agent.

10. A composition according to claim 1 comprising 0.1-10 wt.% of the Formula I compound and 0.25-33 wt.% of a sunscreening agent.

11. A composition according to claim 1 comprising 0.1-10 wt.% of the Formula I compound and 1-12 wt.% of a tanning agent.

12. A composition according to claim 1 comprising 0.1-10 wt.% of the Formula I compound and 1-12 wt.% of a cleansing agent.

13. A composition according to claim 1 which is a makeup comprising 0.01-5 wt.% of the Formula I compound and 1-40% of a cosmetically acceptable pigment.

14. A composition according to claim 1 comprising 0.1-10 wt.% of the Formula I compound and 0.1-50% of a protein.

15. A process for cosmetically terating an external portion of the human body by cosmetically applying thereto a cosmetic composition comprising up to 25 wt% of a compound of the formula

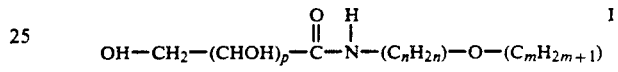

wherein p is a whole number from 1 to about 4, $(C_nH_{2n})$ is a straight or branched chain alkyl bridge in which n is a whole number of 1 to about 6, and $(C_mH_{2m+1})$ is a straight or branched chain alkyl group in which m is a whole number of 1 to about 6.

16. A process according to claim 15, wherein the compound in said composition is methoxy propyl gluconamide.

17. A process for moisturizing and softening human skin by the application thereto of a cosmetic composition selected from the group consisting of lotion, cream, ointment, and make-up base containing a cosmetically acceptable pigment, comprising up to 25 wt% of one or more compounds of the formula

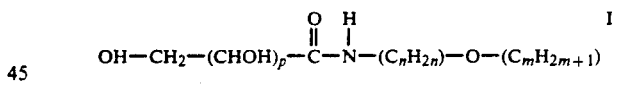

wherein p is a whole number from 1 to about 4, $(C_nH_{2n})$ is a straight or branched chain alkyl bridge in which n is a whole number of 1 to about 6, and $(C_mH_{2m+1})$ is a straight or branched chain alkyl group in which m is a whole number of 1 to about 6.

18. A process according to claim 17 wherein the compound in said composition is methoxy propyl gluconamide.

* * * * *